United States Patent [19]
Liu et al.

[11] Patent Number: 5,772,888
[45] Date of Patent: Jun. 30, 1998

[54] SEPARATION AND/OR CONCENTRATION OF AN ANALYTE FROM A MIXTURE USING A TWO-PHASE AQUEOUS MICELLAR SYSTEM

[75] Inventors: Chia-Li Liu, Cambridge; Daniel Blankschtein, Brookline, both of Mass.

[73] Assignee: Massachusetts Institute of Technology, Cambridge, Mass.

[21] Appl. No.: 683,233

[22] Filed: Jul. 18, 1996

Related U.S. Application Data

[60] Provisional applications No. 60/001,549, Jul. 27, 1995 and 60/018,379 May 29, 1996.

[51] Int. Cl.[6] ..................................................... B01D 11/04
[52] U.S. Cl. ........................... 210/634; 210/638; 210/639
[58] Field of Search .................................. 210/634, 638, 210/639; 530/412, 422

[56] References Cited

U.S. PATENT DOCUMENTS

| | | | |
|---|---|---|---|
| 4,725,358 | 2/1988 | Ananthapadmanabhan | 210/639 |
| 4,808,314 | 2/1989 | Karplus | 210/639 |
| 4,909,940 | 3/1990 | Horowitz | 210/634 |
| 5,266,205 | 11/1993 | Fulton | 210/639 |

OTHER PUBLICATIONS

Harrison et al., *Journal of Cell Science*, 102, 123–132 (1992).
Bordier, *The Journal of Biological Chemistry*, 256, 1604–1607 (1981).
Terstappen et al., *Journal of Biotechnology*, 28, 263–275 (1993).
Sanchez–Ferrer, et al., *Critical Reviews in Biochemistry and Molecular Biology*,29, 275–313 (1994).
Hooper et al., *Biochem. Journal*, 280, 745–751 (1991).
Cole, *Biotechniques*, 11, 18–24 (1991).
Werck–Reichhart et al., *Analytical Biochemistry*, 197, 125–131 (1991).
Saitoh et al., *Talanta*, 42, 119–127 (1995).
Saitoh et al., *Trends in Anal. Chem.*, 14, 213–217 (1995).
Nikas et al., *Macromolecules*, 25, 4797–4806 (1992).
Liu et al., *AIChE Journal*, 41, 991–995 (1995).
Hinze et al., Critical Reviews in Analytical Chemistry, 24, 133–177 (1993).
Helenius and Simons,*The Journal of Biological Chemistry*, 247, 3656–3661 (1972).
Makino et al., *The Journal of Biological Chemistry*, 248, 4926–4932 (1973).
Puvvada and Blankschtein, The Journal of Biological Chemistry, 92, 3710–3724 (1990).
Naor et al, *The Journal of Physical Chemistry*, 96, 7830–7832 (1992).
Abbott et al., *Bioseparation*, 1, 191–225 (1990).
Dubin and Principi, *Journal of Chromatography*, 479, 159–164 (1989).

*Primary Examiner*—Ernest G. Therkorn
*Attorney, Agent, or Firm*—Bromberg & Sunstein LLP

[57] ABSTRACT

The present invention provides a method, device and diagnostic kit for separating and/or concentrating an analyte from a mixture containing one or more contaminants according to size using a two-phase aqueous micellar system. The methods and devices are applicable to a wide range of analytes including environmental pollutants and biological materials. Conditions for optimizing size separation of analyte and contaminant are provided and include selection of a single surfactant type or surfactant mixture, surfactant concentration and composition, temperature, pH, salt type and concentration, and the addition of polymers. The separation or concentration efficiencies can be further enhanced by repeatedly generating the two-phase aqueous systems in a multi-stage operation. This invention can be used for removing viruses from proteins following fermentation processes, as well as for concentrating viruses for vaccine manufacturing or gene therapy.

65 Claims, 8 Drawing Sheets

SEPARATION AND/OR CONCENTRATION OF AN ANALYTE FROM A MIXTURE USING A TWO-PHASE AQUEOUS MICELLAR SYSTEM

RELATED APPLICATIONS

This application claims the benefit of the earlier filing dates of U.S. provisional patent application Ser. No. 60/0001,549, filed Jul. 27, 1995 and Ser. No. 60/018,379 filed May 29, 1996.

TECHNICAL FIELD

The present invention relates to the separation and/or concentration of an analyte using a two-phase aqueous micellar system.

BACKGROUND OF THE INVENTION

One of the critical steps in the manufacturing of biological materials or chemical compounds is the isolation and purification of the desired material from a complex medium. For example, in the cases of proteins or virus particles produced or generated through fermentation, separation or concentration of the desired material from contaminating materials in large-scale manufacturing is always necessary. In addition, preparation of purified molecules generated by chemical synthesis or extracted from natural materials also requires purification or concentration steps that are often complex, time consuming, and costly.

Commonly used separation methodologies include centrifugation, chromatography, and membrane filtration. However, centrifugation, which utilizes a density gradient, may disrupt the structure of biomolecules, and the capability of scaling up the centrifugation operation is limited. Chromatography, which achieves separation based on the difference in particle size, electrostatic interactions, or specific interactions such as affinity ligands, can achieve high separation efficiency, but is not easily scaled up. In addition, the preparation procedures involved in the chromatography operation, including preparation of the eluent solutions and packing of the columns, are tedious. Membrane filtration is easy to operate, but it may involve the application of pressure, which may be detrimental to certain materials.

Other separation methodologies include two-phase liquid-liquid extraction methods. The traditional liquid-liquid extraction method utilizes two immiscible phases formed by contacting an organic phase with an aqueous phase. The analyte is separated according to its solubility in one of the two phases, or alternatively, it is precipitated at the interface. The disadvantage of this approach follows from the possible adverse effects of an organic solvent on the conformations and functions of biological molecules.

An alternative liquid-liquid extraction method utilizes two-phase aqueous systems formed by using water-soluble polymers. Certain aqueous solutions containing two types of water-soluble polymers will separate into two coexisting phases, with each phase containing predominantly only one type of polymer.

The most commonly used polymers are dextran and poly(ethylene oxide). The use of this type of systems is exemplified by Harrison et al. (*J. Cell. Sci.*, 102, 123–132, 1992) who reported the concentration of spermatozoa by these means.

Another approach using a two-phase aqueous system relies on the ability of surfactants to form micelles. Surfactants are molecules composed of a hydrophilic moiety, which is soluble in water, and a hydrophobic moiety, which is not. This duality towards an aqueous environment leads to a broad spectrum of complex self-association phenomena which simple solutes do not exhibit in water. In order to avoid contact of the hydrophobic moieties with water, the individual surfactant molecules self-associate to form aggregate structures known as micelles. Whereas these micelles are hydrophilic on the exterior surface, they possess a hydrophobic and non-aqueous core. Typically, micellization, that is, the formation of micelles, occurs beyond a threshold surfactant concentration, known as the critical micellar concentration (CMC), below which surfactant molecules are predominantly dispersed as monomers and above which they begin to form micelles.

The dual hydrophobic/hydrophilic environment provided by micelles has been exploited to separate and concentrate biological molecules according to their hydrophobicity using an aqueous solution of the non-ionic surfactant Triton X-114, which, under certain conditions, separates into two phases. In this system, the biological materials are concentrated in the phase containing a high concentration of micelles with the more hydrophobic analytes being separated from the contaminants by incorporation into the cores of the micelles. (Bordier (*J. Biol. Chem.*, 256, 1604–1607, 1981); Terstappen et al. (*J. Biotechnol.*, 28, 263–275, 1993); Sanchez-Ferrer et al. (*Crit. Rev. Biochem. Mol. Biol.*, 29, 275–313, 1994); Hooper et al., (*Biochem. J.*, 280, 745–751, 1991); Cole (*Biotechniques*, 11, 20–24, 1991); Werck Reichhart et al. (*Anal. Biochem.*, 197, 125–131, 1991); Saitoh et al. (*Talanta*, 42, 119–127, 1995; *Trends in analytical chemistry*, 14, 213–217, 1995). In order to further purify the hydrophobic material separated in this way, a series of extraction steps may be required to extract the analyte which has been incorporated within the micelles. Based on the principles laid out by Bordier (1981) in which the hydrophobic proteins may be incorporated into the core of micelles in the micelle-rich phase of a two-phase aqueous system, Saitoh et al. (*Talanta*, 42, 119–127, 1995) developed a method for also retrieving hydrophilic proteins in the micelle-rich phase by causing the hydrophilic proteins to be retained by ligands on the surface of micelles.

In all the above references, the experimental conditions are driven by the theory that a material of interest be separated according to its degree of hydrophobicity. Accordingly, hydrophobic materials are concentrated in the micelle-rich phase, and the remainder of material, considered to be waste, passes into the second phase of the two-phase aqueous system, identified in the above references as the aqueous phase. This theory is substantially different from that disclosed by Nikas et al. (*Macromolecules*, 25, 4797–4806, 1992, ); and Liu et al. (*AIChE J.*, 41, 991–995, 1995), these being incorporated by reference, who identified a principle of separation that relies on volume exclusion and not on the degree of hydrophobicity, where the analyte could be partitioned into the second phase of the two-phase aqueous system, identified as micelle-poor and not as aqueous as previously described (see above). According to Nikas et al. and Liu et al., the volume exclusion of molecules from the micelle-rich phase could be enhanced by using preselected micelle shapes. Nikas et al. and Liu et al. supported their theory of volume exclusion by describing the partitioning behavior of preparations containing single hydrophilic proteins in aqueous micellar phases containing cylindrical micelles.

There is a need for identifying effective methods of separating or concentrating an analyte from a mixture where the methods are simple to implement, do not involve denaturing steps, are applicable to a wide range of materials, and can be easily scaled up.

SUMMARY OF THE INVENTION

This invention satisfies the above need.

A preferred embodiment of the present invention is a method for size separating a mixture of reagents including an analyte and at least one contaminant of different size, including the following steps: providing at least one surfactant, the surfactant being capable under selected conditions of forming a two-phase aqueous micellar system having a micelle-rich phase and a micelle-poor phase; forming the two-phase aqueous micellar system containing surfactant as descibed above in the presence of the mixture of reagents; and permitting the analyte and the contaminant to partition unevenly between the two phases so as to cause at least partial separation of the analyte from the contaminant on the basis of size.

According to embodiments of the invention, the analyte includes environmental contaminants, biological materials or colloidal particles, where biological materials further include any of pathogens, bacteria, viruses, cells, organelles, blood products, protein aggregates, dispersed proteins including hydrophilic proteins, and nucleic acids including plasmids.

According to embodiments of the invention, the surfactant may include non-ionic surfactants, such as alkyl poly (ethylene oxide), or zwitterionic (dipolar) surfactants, such as dioctanoyl phosphatidylcholine, and ionic, zwitterionic, and non-ionic surfactant type ligands, or a mixture of any of the foregoing.

According to embodiments of the invention, conditions are selected for optimal separation or concentration of analyte that may include an overall surfactant concentration of 1–30 wt %, a temperature lower than 100° C., a solution pH of 2–12, salt type including alkali salts, phosphate, sulphate, citrate, or nitrate salts at a concentration of 0–5M, and in certain circumstances, the addition of polymers. For example, the conditions for forming a two-phase aqueous micellar system, composed of the non-ionic surfactant n-decyl tetra(ethylene oxide) ($C_{10}E_4$), that are suitable for separating mixtures, include but are not limited to a final $C_{10}E_4$ concentration in the range of 1–8 wt %, a temperature above 18° C., a pH in the range of 5–9, and may further include salts such as alkali salts, phosphate, sulphate, citrate, and nitrate salts having a final concentration in the range of 0–5M. In the case of the two-phase aqueous micellar system composed of the zwitterionic surfactant dioctanoyl phosphatidylcholine ($C_8$-lecithin), the conditions for generating the two-phase aqueous system include, but are not limited to, a final $C_8$-lecithin concentration in the range of 1–10 wt %, a temperature lower than 100° C., a pH in the range of 5–9, and may further include the addition of salts such as alkali salts, phosphate, sulphate, citrate, and nitrate salts having a final concentration in the range of 0–5M.

According to embodiments of the invention, conditions may be selected that cause individual micelles to be cylindrical or spherical.

A further embodiment of the invention is a diagnostic kit for assaying an analyte, that includes a known amount of surfactant for adding to a liquid sample containing the analyte, such that the surfactant is capable of forming a two-phase aqueous micellar system, wherein the analyte becomes concentrated in one of the two coexisting micellar phases; and means for determining the concentration of the analyte.

A further embodiment of the invention is a device for separating an analyte from at least one contaminating material in a solution, including a reaction chamber, having a first port for admitting a known amount of surfactant and a sample containing the analyte in the presence of contaminating material, and a second port for accessing analyte after separation from contaminating materials; a means for regulating solution conditions in the reaction chamber such as pH and temperature; and a two-phase aqueous micellar system contained within the reaction chamber.

A further embodiment of the invention is a method for purifying virus from a mixture containing contaminants, including the steps of providing at least one surfactant, the surfactant being capable under selected conditions of forming a two-phase aqueous micellar system having a micelle-rich phase and a micelle-poor phase; forming the two-phase aqueous micellar system containing surfactant as specified above in the presence of the mixture of reagents; and permitting the virus and the contaminant to partition unevenly between the two phases so as to cause at least partial separation of the virus from the contaminant on the basis of size.

The area beneath the data-point curve is the two-phase region, in which the partitioning experiments were conducted.

Figure 3:
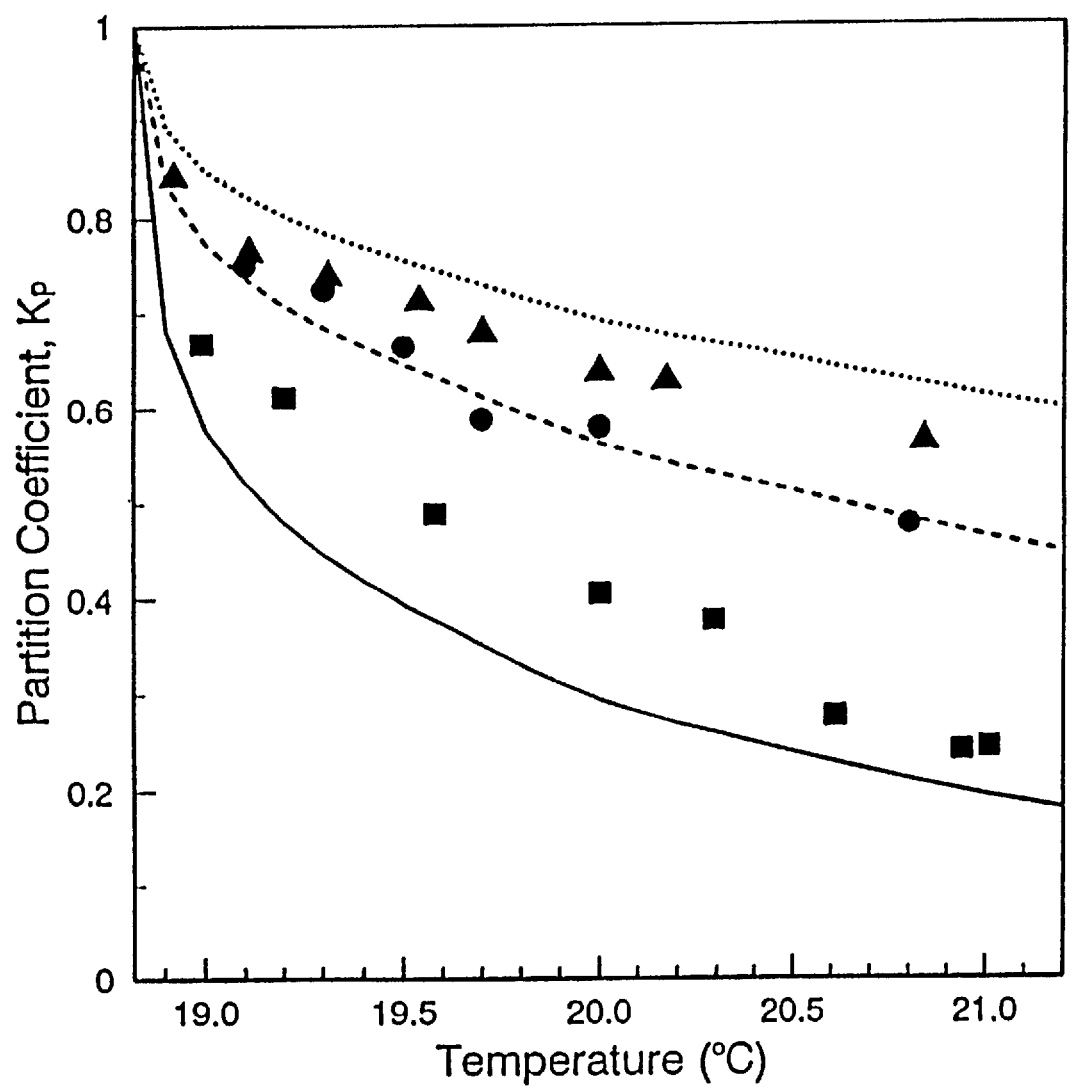

FIG. 3 shows the experimentally measured partition coefficient, $K_p$, of cytochrome c (▲), ovalbumin (●), and catalase (■) in the temperature range of 18.8°–21.2° C. in the two-phase aqueous $C_{10}E_4$ micellar system. Also shown are the predicted partition coefficients of cytochrome c (•••), ovalbumin (- -), and catalase (—) as a function of temperature.

Figure 4:
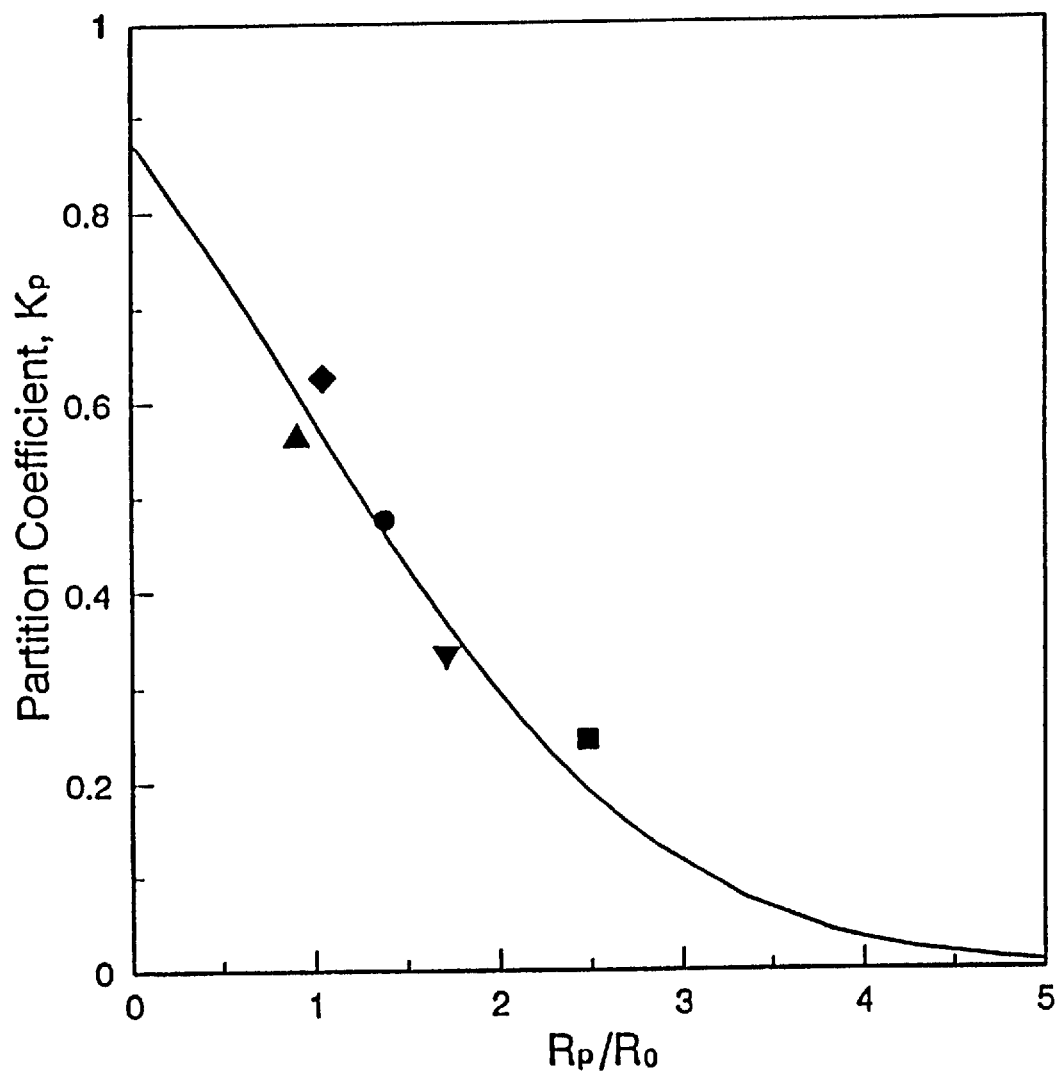

FIG. 4 shows the predicted partition coefficient, $K_p$, as a function of the ratio, $R_p/R_0$, in the two-phase aqueous $C_{10}E_4$ micellar system at 21° C. $R_p$ is the protein hydrodynamic radius, $R_0$=21 Å is the cross-sectional radius of a $C_{10}E_4$ cylindrical micelle. The various symbols correspond to the experimentally measured $K_p$ values of the following proteins: cytochrome c (▲, $R_p$=19 Å), soybean trypsin inhibitor (♦, $R_p$=22 Å), ovalbumin (●, $R_p$=29 Å), bovine serum albumin (▼, $R_p$=36 Å), and catalase (■, $R_p$=52 Å).

Figure 5:
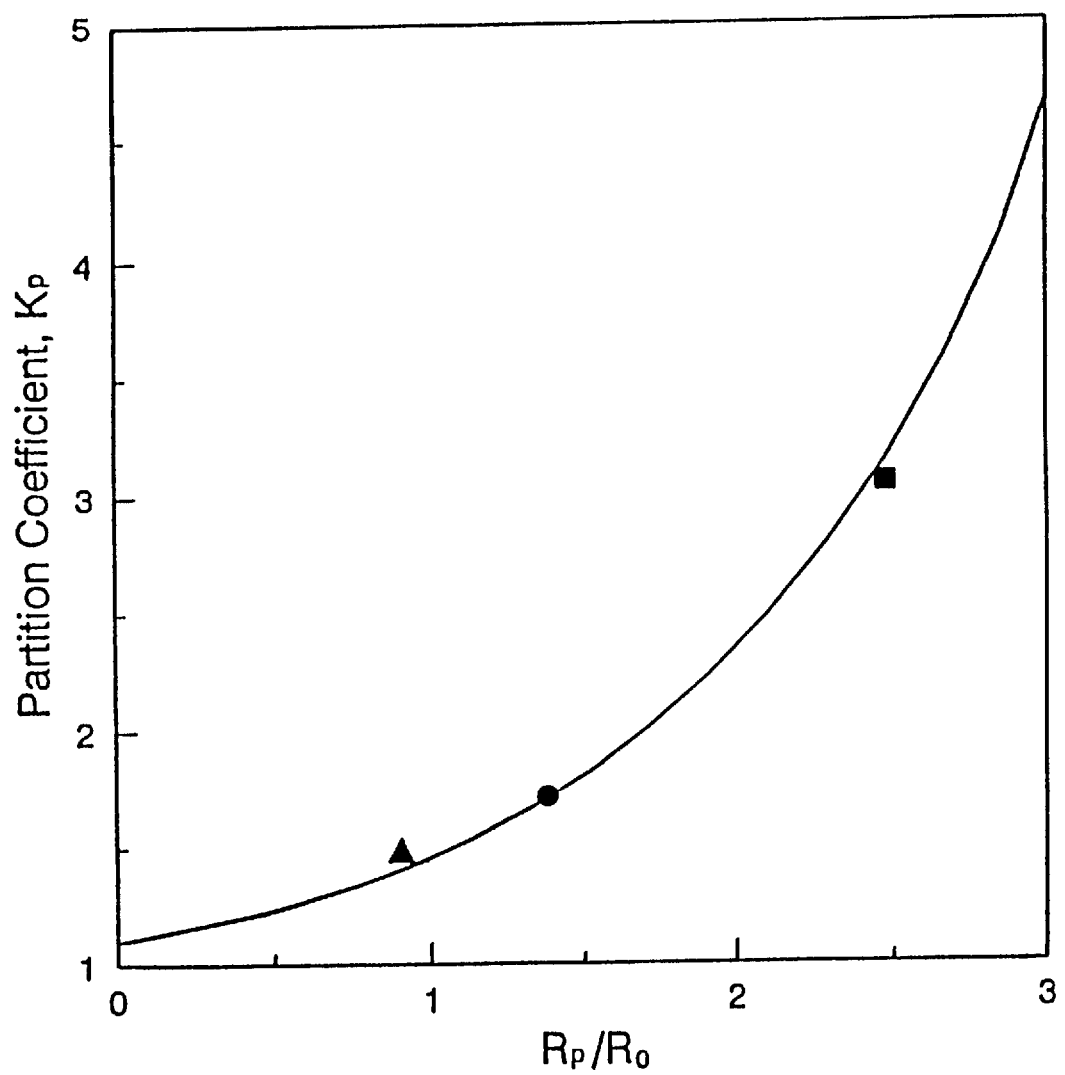

FIG. 5 shows the predicted partition coefficient, $K_p$, as a function of the ratio, $R_p/R_0$, in the two-phase aqueous $C_8$-lecithin micellar system at 10° C. $R_p$ is the protein hydrodynamic radius, $R_0$=21 Å is the cross-sectional radius of a $C_8$-lecithin cylindrical micelle. The various symbols correspond to the experimentally measured $K_p$ values of the following proteins: cytochrome c (▲, $R_p$=19 Å), ovalbumin (●, $R_p$=29 Å), and catalase (■, $R_p$=52 Å).

Figure 6:
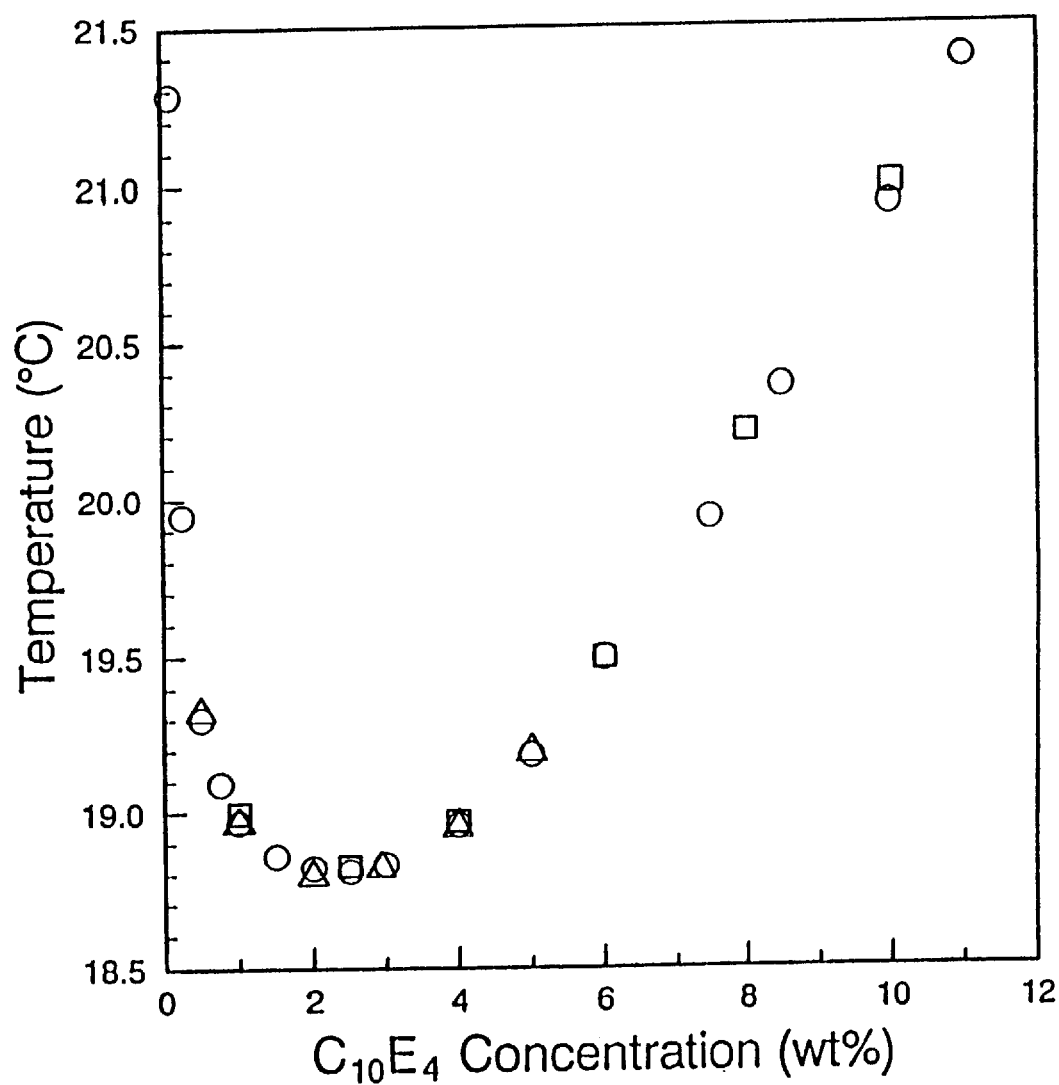

FIG. 6 shows the experimentally measured coexistence (cloud-point) curves of the $C_{10}E_4$-buffer micellar system without bacteriophage (○), with P22 at a concentration of $10^8$ particles/mL (Δ), and with T4 at a concentration of $2\times10^8$ particles/mL (□).

Figure 7:
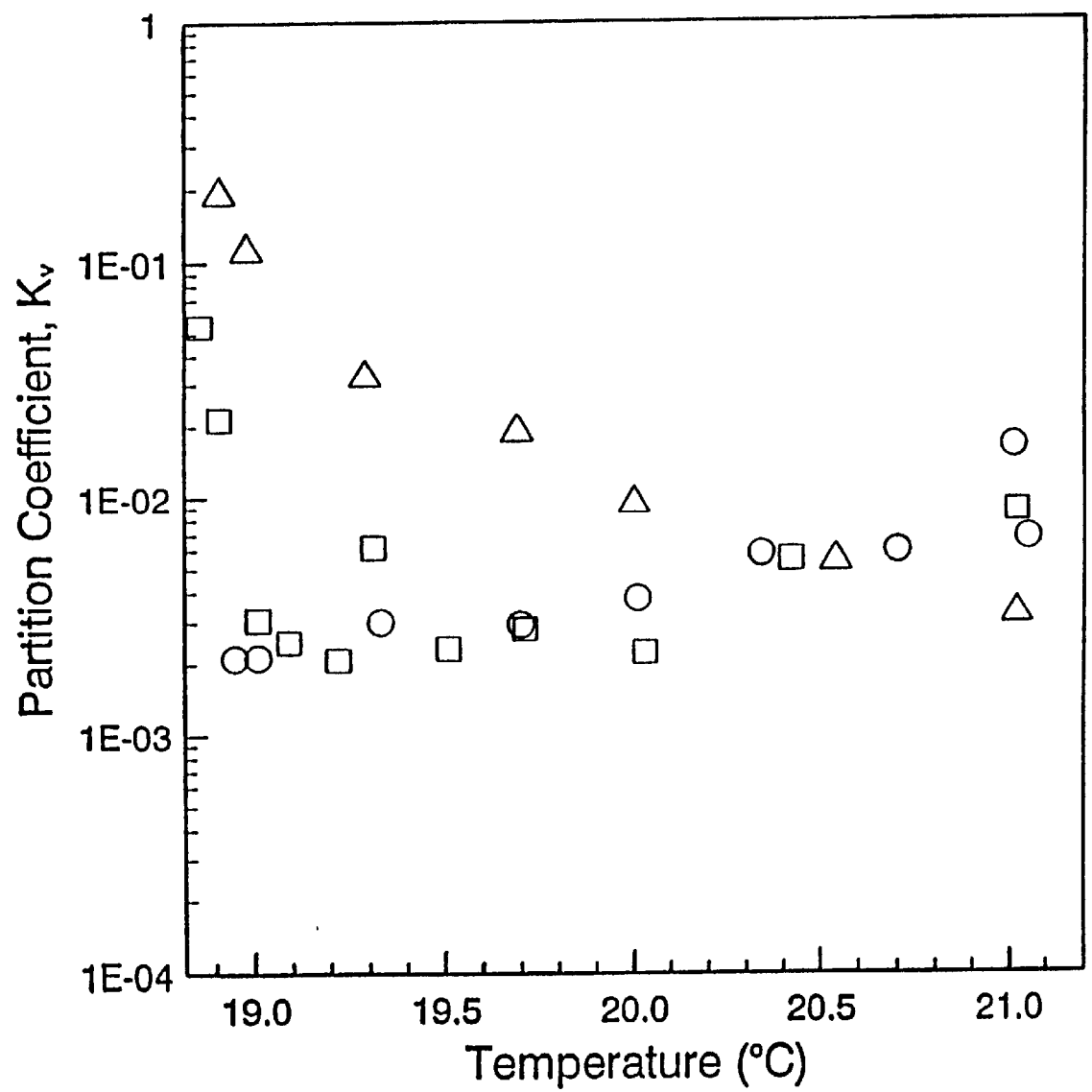

FIG. 7 shows the experimentally measured partition coefficient, $K_v$, of the bacteriophages φX174 (Δ), P22 (□), and T4 (○), in the two-phase aqueous $C_{10}E_4$ micellar system in the temperature range of 18.8°–21.2° C.

Figure 8:
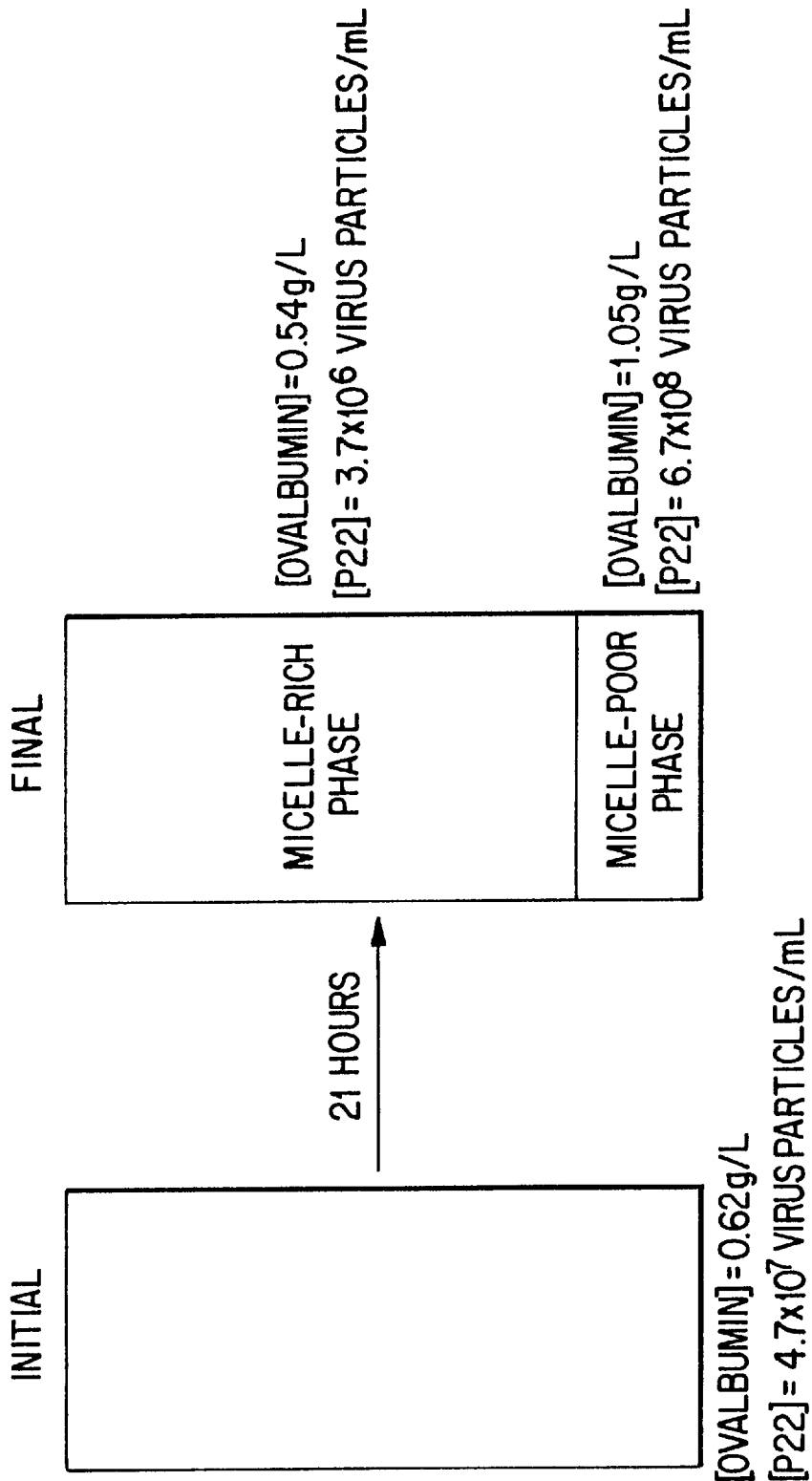

FIG. 8 shows a schematic illustration of the unequal-volume partitioning experiment conducted at 20° C., in which the final volume ratio obtained was $V_t/V_b=14.5$.

DETAILED DESCRIPTION OF SPECIFIC EMBODIMENTS

In the preferred embodiment of the invention, a method is provided for separating and/or concentrating an analyte or a contaminant from a mixture according to size. The method utilizes a two-phase aqueous environment formed by micelles that is non-disruptive to biological structure and function.

The analyte as used here and in the claims is defined as a specific molecule, compound, particle, cell, or colloid that is required to be separated from other materials for any purpose including analysis, purification, concentration or other use. Specific examples of analytes include environmental pollutants, biological materials such as pathogens, viruses, proteins, nucleic acids including DNA, RNA, plasmids, cells, or cell organelles, blood products, protein aggregates, organic material, or inorganic material.

The aqueous micellar system as used here and in the claims is defined as an aqueous solution containing self-associating aggregates of surfactant molecules (micelles), the surfactant molecules being composed of a hydrophilic moiety, which is soluble in water, and a hydrophobic moiety, which is not. The cloud-point temperature as used here and in the claims is defined as the temperature at which phase separation of the micellar solution begins to occur. The cloud-point temperature depends on the overall surfactant concentration, as well as on other solution conditions, such as salt type and concentration and solution pH.

The partition coefficient of an analyte, K, as used here and in the claims is defined as the ratio of the analyte concentration in the top phase, $C_t$, to that in the bottom phase, $C_b$, that is, $K=C_t/C_b$.

We elected to apply the principle of excluded-volume interactions (Nikas et al. (1992)) to separate mixtures of analytes and contaminating materials on the basis of size in two-phase aqueous micellar systems. Accordingly, we identified conditions suitable for driving the majority of the larger reagent in a mixture into the aqueous domain of the micelle-poor phase and the majority of the smaller reagents in the mixture into the aqueous domain of the micelle-rich phase.

The invention is fundamentally different from the generally accepted art which requires separating and concentrating molecules in the micellar domain of the micelle-rich phase of a two-phase aqueous micellar system according to the molecule's degree of hydrophobicity (Hinze et al., Critical Reviews in Analytical Chemistry, 24, 133–177, 1993).

The principle of separation according to the invention is depicted by the graph in FIG. 4, and the consequences are depicted schematically in FIG. 8 which exemplifies the separation outcome for a virus particle (P22) and a protein (ovalbumin) mixture in the non-ionic $C_{10}E_4$ two-phase aqueous micellar system. Examples of conditions under which P22 (the large reagent) migrated predominantly to the micelle-poor phase while ovalbumin (the small reagent) remained predominantly in the micelle-rich phase are provided in Example 3.

The extent of the migration of differently-sized molecules or particles can be selectively altered according to the conditions under which the two-phase aqueous micellar system has been formed. According to an embodiment of the invention, it is desirable to select conditions which minimize the extent to which the smaller reagent moves into the micelle-poor phase, while permitting the larger reagent to migrate into the micelle-poor phase in an unimpeded manner so as to optimize the separation. Furthermore, where it is desirable to concentrate a reagent in the micelle-poor phase, conditions have been provided that minimize the volume of the micelle-poor phase.

The conditions under which a two-phase aqueous micellar system may be formed so as to maximize the differences in the extent of migration of different-sized materials to the micelle-poor phase include: the selection of the surfactant molecular structure, the manipulation of temperature, pH, and salt conditions, as well as the addition of polymers and other types of surfactants, and the presence of micelle-associated ligands suitable for retarding the extent of migration of the 'smaller' reagent into the micelle-poor phase thereby increasing the partition coefficient difference of 'larger' and 'smaller' reagents beyond that shown in FIG. 4. Manipulation of these parameters can provide substantially enhanced separation and/or concentration of analyte, such as viruses, from contaminating materials, such as hydrophilic proteins.

The conditions under which the separation is best achieved, vary according to the surfactant used. For example, typical condition ranges include temperatures lower than the boiling point of the surfactant solution at atmospheric pressure, more particularly less than 100° C., more particularly 4°–50° C., concentration of surfactant of 1–30wt %, a pH range of 2–12, and salts selected from alkali salts, phosphates, sulfates, citrate, and nitrate salts at concentrations of 0–5M. These ranges of values are given as guidelines but do not exclude conditions outside these ranges that may be found to be optimal for selected surfactants for purposes of separation or concentration according to embodiments of the claimed invention.

The method of the invention may utilize any single surfactant or mixture of surfactants known in the art including those described in Table 1 of Hinze et al., (1993) and incorporated here by reference, so as to achieve separation of a mixture of reagents. These surfactants may be non-ionic, zwitterionic, or ionic.

Additionally, these surfactants may have a binding affinity to at least one of the reagents in the mixture or may be associated with ligands that have a binding affinity to at least one of the reagents. This binding affinity may arise through any type of nonionic or ionic linkages including van der Waals forces, hydrogen bonding, covalent binding, and ionic associations.

Non-Ionic and Zwitterionic Surfactants Used for Generating Aqueous Micellar Solutions.

Non-ionic and zwitterionic surfactants are known to be gentle and mild to biological materials (Helenius and Simons, *J. Biol. Chem.*, 247, 3656–3661, 1972; Makino et al., *J. Biol. Chem.*, 248, 4926–4932, 1973). Accordingly, the two-phase aqueous micellar systems composed of non-ionic and zwitterionic surfactants are particularly suitable for separation or concentration of biological materials.

In embodiments of the invention, the nonionic surfactant $C_{10}E_4$ and the zwitterionic surfactant $C_8$-lecithin have been used separately to generate two-phase aqueous micellar systems for purposes of separating and concentrating biological molecules. These surfactants were selected because of the following desirable properties: having a nondenaturing effect on protein molecules; being capable of forming a two-phase aqueous micellar system over a convenient temperature range; being chemically homogeneous; and not interfering with detection methods used to measure biomolecule concentrations, specifically those of proteins.

The non-ionic surfactant n-decyl tetra(ethylene oxide) ($C_{10}E_4$) belongs to the family of alkyl poly(ethylene oxide) ($C_iE_j$) surfactants, which possess a hydrophilic part consisting of j ethylene oxide (E=$CH_2CH_2O$) units and a linear saturated hydrocarbon chain consisting of i carbon atoms as the hydrophobic part. Accordingly, the surfactant $C_{10}E_4$ has the following chemical formula:

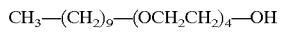

$$CH_3-(CH_2)_9-(OCH_2CH_2)_4-OH$$

The CMC of $C_{10}E_4$ aqueous solutions is $6.4 \times 10^{-4}$M at 20.5° C. The $C_{10}E_4$ aqueous micellar system exhibits a lower consolute point, that is, phase separation in this system is induced by increasing temperature (see FIG. 1). The critical temperature, $T_c$ (that is, the temperature corresponding to the minimum of the coexistence curve in FIG. 1) of the $C_{10}E_4$-water system, is about 19° C. in pH 7 McIlvaine buffer at a critical surfactant concentration $X_c$ (that is, the surfactant concentration corresponding to $T_c$, which is about 2.5 wt % in FIG. 1). It is noteworthy that $C_{10}E_4$ micelles exhibit significant one-dimensional growth into cylindrical structures (with increasing temperature or surfactant concentration).

The zwitterionic surfactant, dioctanoyl phosphatidylcholine ($C_8$-lecithin), comprises a hydrophobic part consisting of two saturated hydrocarbon chains attached to a glycerol moiety, and a hydrophilic part consisting of a phosphatidylcholine group which is zwitterionic at a pH condition of 3–11, implying that the net charge of the hydrophilic part is zero over this pH range.

The CMC of $C_8$-lecithin aqueous solutions is $2.5 \times 10^{-4}$M at 48° C. The aqueous micellar system of $C_8$-lecithin exhibits an upper consolute point, and phase separation is thus induced by lowering the temperature (see FIG. 2). The critical point of the $C_8$-lecithin-water micellar system is characterized by $T_c \approx 47°$ C. and $X_c=2.77$ wt % (see FIG. 2). Similar to the $C_{10}E_4$-water system, micelles of $C_8$-lecithin exhibit significant one-dimensional growth into cylindrical structures with decreasing temperature and increasing surfactant concentration.

Applications of a Two-Phase Aqueous Micellar System for Separation or Concentration of Analytes from Mixtures.

An example of an application of the invention is the removal of contaminating viruses from a desired protein species, a major practical problem in the biotechnology field. In this case, starting with a solution containing both proteins and large virus particles, it is possible to remove (clear) substantially all or a large fraction of the viruses from the micelle-rich phase, while retaining the majority of the proteins in that phase (see Examples 3 & 4)

We have identified conditions suitable for partitioning mixtures including large hydrophilic particles such as viruses, including φX174, P22, and T4, using a two-phase aqueous micellar system, in particular, that composed of the nonionic surfactant $C_{10}E_4$ (see Example 3). Although both the hydrophilic proteins and the viruses were found to partition preferentially into the micelle-poor phase of the two-phase aqueous $C_{10}E_4$ micellar system, the viruses were found to have a much stronger tendency to do so.

One of the strategies used here for enhancing the separation and concentration efficiencies of reagents in a two-phase aqueous micellar system is to manipulate the volume ratio of the two coexisting phases (see Example 3).

Specifically, we found that when the volume of the micelle-rich phase is caused to be larger than that of the micelle-poor phase, the overall separation and concentration efficiencies were enhanced. According to Example 3, most of the virus moved into the small micelle-poor phase, and most of the protein remained in the large micelle-rich phase, so that the virus was concentrated in the small volume micelle-poor phase.

The method of the invention provides a rapid, simple and efficient means to separate and/or concentrate mixtures of materials. The method is relatively simple to scale up, simple to operate, and is relatively non-destructive for biological materials. Examples of reagents that may be separated and/or concentrated using this method include hydrophilic proteins, viruses, protein aggregates, blood products, nucleic acids including DNA, ribonucleoproteins, RNA molecules, and plasmids, cells, cell fragments and other biological materials. The method may also be utilized to separate environmental contaminants such as metal ions, radioactive contaminants and synthetic organic materials.

The method of the invention is also well suited for concentrating viruses from various solutions, including sewage water, and body fluids, where the initial virus concentration may be too low to be effectively assayed, or where the presence of other materials may interfere with viral detection. Using this method, detection and assaying of viruses can be facilitated. Improved diagnosis of viral infections and diseases may follow, as, for example, in the diagnosis of infantile diarrhea caused by rotaviruses where concentration of these viruses from the excrement of infants is desirable.

The method of the invention is also well suited for concentrating viruses during manufacturing, such as is required in vaccine production and in preparation of viruses for gene therapy. Such viruses can be purified and/or concentrated from supernatant or cellular debris in a convenient and cost-effective manner.

In the separation or concentration of analytes such as viruses as outlined above, surfactant may be added at the selected temperature to the solution containing the analyte to obtain a suitable final concentration of surfactant for forming a two-phase aqueous micellar system. Additional reagents may also be added to achieve the appropriate pH and salt concentrations for optimal separation of analyte or concentration of the analyte. Alternatively, a mixture of analyte and contaminating material may be added to the two-phase aqueous micellar system already formed from a surfactant solution.

Another application includes the removal of protein aggregates from the desired protein monomers. These aggregates may form as a result of shearing forces arising during protein purification processes, leading to loss of protein yield and biological activity. The efficient removal of these protein aggregates is an important step in the protein purification process. This may be achieved by exploiting the size difference between the protein aggregates and the desired protein "monomers", as well as by utilizing electrostatic interactions and/or the specific affinity of the protein to surfactant ligands discussed below.

Whereas the conditions under which the analyte is concentrated may be the same as the conditions under which the analyte is separated from contaminating material, in certain circumstances, the optimal conditions under which the analyte is concentrated may differ from the conditions used for optimal separation. To optimize the concentrating effect of the two-phase aqueous micellar system, it is desirable to minimize the volume of the phase into which the analyte preferentially partitions (see Example 3).

In addition to the separation and concentration methods demonstrated in Examples 1–3, the separation and concentration efficiencies of two-phase aqueous micellar systems can be further enhanced by manipulating other factors (see Example 4).

Mixed Micellar Systems.

Separation and concentration of analyte using a two-phase aqueous micellar system can be enhanced by the use of a mixture of surfactants. By mixing different surfactant species, for example, non-ionic and ionic surfactants, it is possible to generate, in situ, a mixed-micellar system in which the partitioning of materials is driven by the electrostatic interactions. Such a mixture may be formed by adding an ionic or a zwitterionic surfactant to a nonionic aqueous micellar system. By triggering an electrostatic attraction between a desired ionic bioproduct (such as a protein) and the oppositely-charged mixed micelles, the desired bioproduct can partition preferentially into the micelle-rich phase. If the undesired biomaterials (such as viruses or cells) are either not charged or have a net charge of the same sign as that of the mixed micelles, electrostatic repulsions with the mixed micelles may drive these undesired biomaterials into the micelle-poor phase. Furthermore, for undesired biomaterials possessing a large size, such as viruses and cells, excluded-volume interactions will further increase their partitioning into the micelle-poor phase.

As an illustration, for concentrating or separating a desired protein species having a net positive charge, an anionic (negatively charged) surfactant such as sodium dodecyl sulfate (SDS) could be added to a non-ionic surfactant, such as $C_{10}E_4$, aqueous micellar system. For a desired protein species having a net negative charge, a cationic (positively charged) surfactant such as cetyltrimethylammonium bromide (CTAB) could be added to the non-ionic ($C_{10}E_4$)aqueous micellar system. Furthermore, zwitterionic surfactants like alkyl betaines, whose net charge varies with solution pH, can be used to trigger pH-dependant electrostatic interactions (either attractive or repulsive as required).

Another example of mixed-micellar systems that may be used to enhance the separation includes utilizing a surfactant-type ligand, which has high affinity towards a desired material. The combination of a surfactant-type ligand with a surfactant results in a mixed-micellar system in situ. An example of a surfactant-type ligand includes hydrophilic immunoglobulins covalently attached to hydrophobic groups to form surfactant-type antibodies. The surfactant-type antibody may then be mixed with a conventional surfactant to form a two-phase aqueous micellar system in which the separation or concentration efficiencies of the corresponding antigen entities can be significantly enhanced.

In addition to forming mixed micelles, another type of mixture involves adding one or more types of polymers to the micellar systems to further increase the ability to manipulate the separation and concentration efficiencies. The types of polymers best suited for a particular separation include non-ionic polymers, ionic polymers, or a mixture of both ionic and non-ionic polymers.

In cases involving the partitioning of charged materials, such as biological materials, their net charges can be altered by varying the solution pH, and the partitioning behavior of these materials in the charged mixed-micellar systems can thus be manipulated. In addition, by adding different salt types and tuning their concentrations in the solution, the partitioning behavior as well as the separation and concentration efficiencies of charged materials can be further varied.

Multi-Stage Partitioning Operation.

The single-stage partitioning operation, as demonstrated in Example 3, can be repeated to further enhance the separation and concentration efficiencies. For example, it is desirable in certain circumstances to collect the analyte from one phase after partitioning, and to repeat the separation method so as to further increase the purity of the analyte in a single phase (see Examples 4 and 5). Alternatively, it is desirable in certain circumstances to retrieve more analyte from the phase containing the majority of the contaminating materials, or to separate or concentrate a single contaminant in a mixture after the substantial removal of an analyte. In these circumstances, the phase containing the majority of the contaminating materials is collected, and the separation method is repeated by forming a second two-phase system.

For these purposes, the single-stage partitioning operation can be further developed into multi-stage or continuous processes, such as a counter-current distribution (CCD) operation, which may be performed in such a way that, after one partitioning stage, the two coexisting phases are physically separated, followed by contacting the top phase with a fresh bottom phase and contacting the bottom phase with a fresh top phase to make the materials re-partition in the new two-phase systems. A device for separating the analyte from at least one contaminating material suited for two-phase aqueous micellar separation by the multi-stage or continuous manner includes a reaction chamber, a first port for introducing reagent and sample and a second port for removing analyte. Optionally, a thermostat and monitors of pH and other solution conditions (such as ionic strength) may be associated with the device to maintain the controlled conditions.

The number of partitioning stages in a separation procedure depends, at least in part, on the partition coefficient of the materials to be removed or concentrated. Whereas a partition coefficient of $10^{-3}$ is sufficient to achieve a high level of separation in a three-stage process (see Example 4), a partition coefficient of $10^{-5}$ has the effect of yielding still better separation or concentration in only two stages (see Example 5). A partition coefficient smaller than $10^{-5}$ may result in optimal separation and concentration in one stage only.

Diagnostic Kit.

Two-phase aqueous micellar systems as described in embodiments of the invention may be used as diagnostic methods and assembled as a kit. For example, surfactant is added to a sample of body fluid containing a pathogen at low concentrations in a reaction vessel. A two-phase aqueous micellar system is formed with the pathogen becoming at least partially separated from contaminating materials and then concentrated in the micelle-poor phase. A marker such as labelled ligand having specificity towards the pathogen may be present in the micelle-poor phase, for example, adsorbed to the walls of the reaction vessel. Other markers include enzymes, dyes and colored proteins such as cytochrome c and other markers known in the art. These markers may be reacted with the analyte and the color intensity measured by, for example, spectrophotometry. In the example of a viral pathogen, a color change would indicate the amount of the pathogen. Alternate means for determining concentration of the analyte may include measurement of isotopes, chemiluminescence, or biochemical techniques.

EXAMPLE 1
Partitioning of Proteins in Two-Phase Aqueous Micellar Systems.

Materials

Homogeneous $C_{10}E_4$ (lot no. 1006) was obtained from Nikko Chemicals (Tokyo). $C_8$-lecithin powder (lot no. 80PC-34) was obtained from Avanti Polar Lipids, Inc. (Alabaster, Ala.). Cytochrome c (from horse heart), soybean trypsin inhibitor (type I-S), ovalbumin, bovine serum albumin, and catalase (from bovine liver) were obtained from Sigma Chemicals (St. Louis, Mo.). All other chemicals used were of reagent grade. All solutions were prepared using deionized water which had been fed through a Milli-Q ion-exchange system and were buffered at pH 7 by 10 mM citric acid and 20 mM disodium phosphate (McIlvaine buffer). Solutions also contained 0.02% sodium azide to prevent bacterial growth.

Experimental Approach

Coexistence curves for liquid-liquid phase separation of the buffered $C_{10}E_4$ and $C_8$-lecithin solutions without and with added proteins were determined by the cloud-point method (Nikas et al., *Macromolecules*, 25, 4797–4806, 1992, and Liu et al., *AIChE J.*, 41, 991–995, 1995) in order to identify the temperature and surfactant concentration ranges over which the partitioning experiments should be conducted, as well as to investigate the influence of proteins on the phase separation behavior of the micellar solutions.

Figure 1:
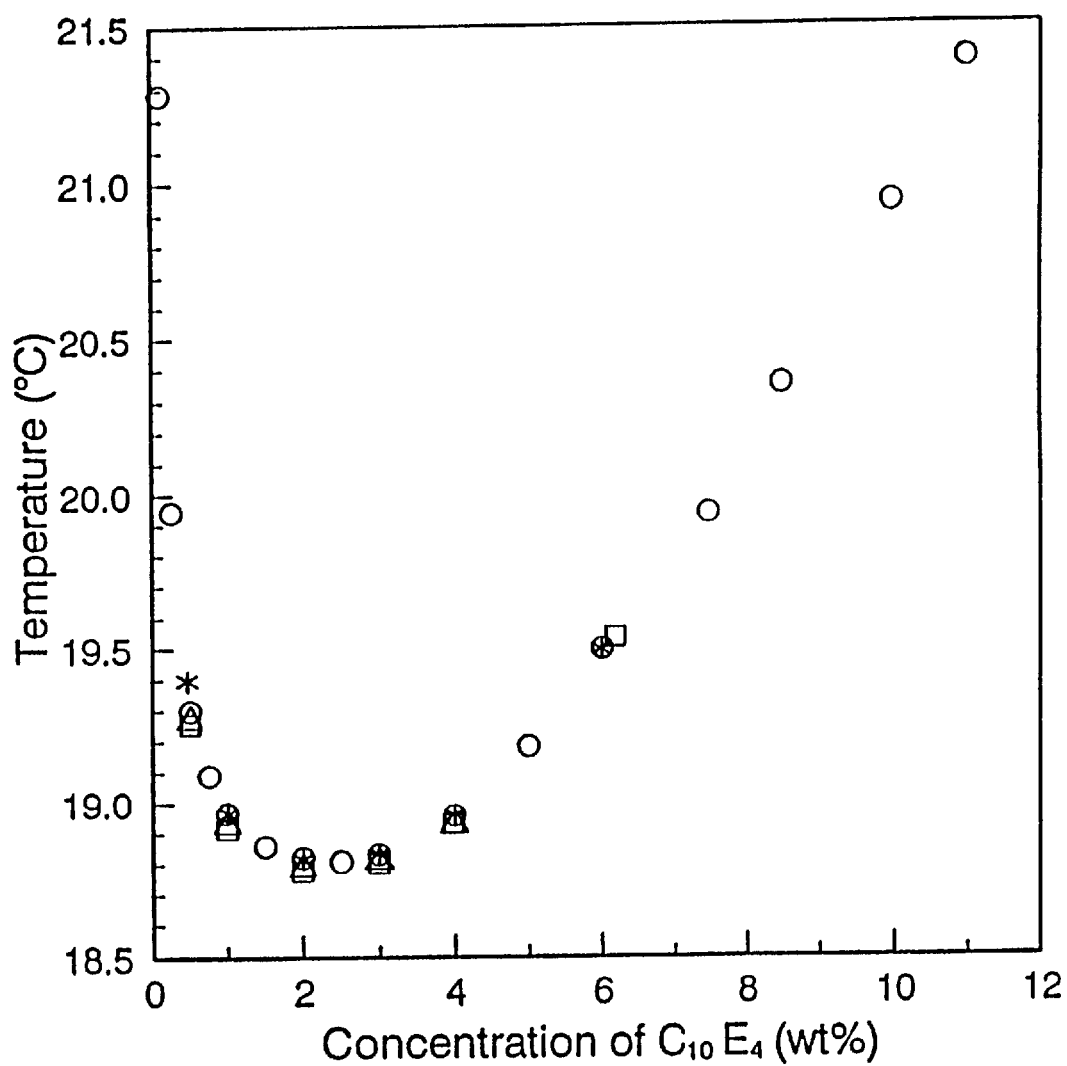
FIG. 1 shows the experimentally measured cloud-point (coexistence) curves of the $C_{10}E_4$ micellar system in pH 7 McIlvaine buffer without protein (○), and with 0.25 g/L cytochrome c (Δ), 0.5 g/L ovalbumin (*), and 0.5 g/L catalase (□). The area above the data-point curve is the two-phase region, in which the partitioning experiments were conducted.
Figure 2:
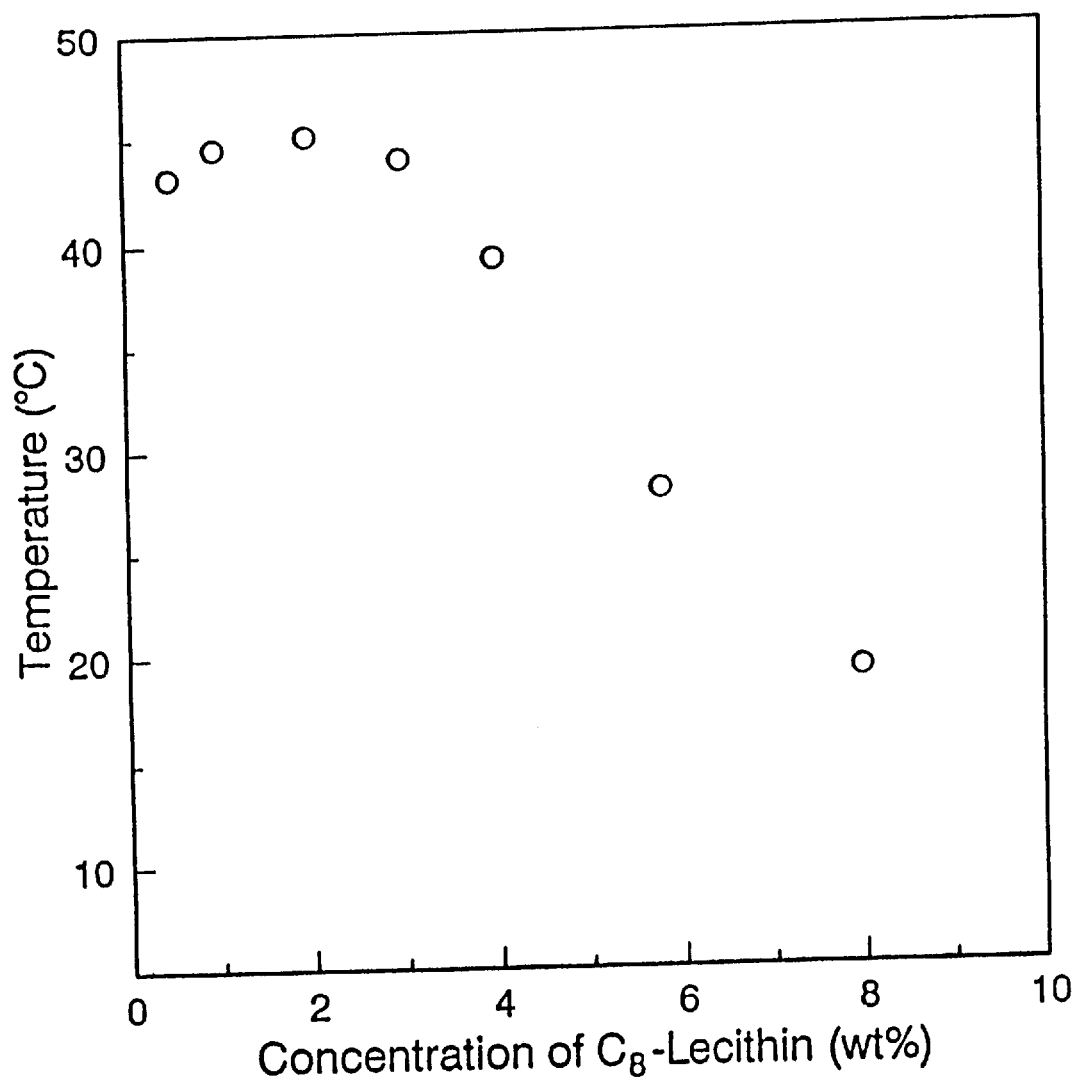
FIG. 2 shows the experimentally measured cloud-point (coexistence) curve of the $C_8$-lecithin micellar system in pH 7McIlvaine buffer without protein (○).

FIG. 1 shows the experimental coexistence curves of the aqueous $C_{10}E_4$ micellar system without protein (○) and with 0.25 g/L cytochrome c (△), 0.5 g/L ovalbumin (*), and 0.5 g/L catalase (□) in pH 7 McIlvaine buffer. The area above the data-point curve is the two-phase region. This figure indicates that: (1) the $C_{10}E_4$ aqueous micellar system phase separates at above 18.8° C., and (2) over the range of surfactant concentrations examined, the added proteins have a negligible effect on the phase separation equilibrium of the $C_{10}E_4$ solutions. The experimental coexistence curve of the $C_8$-lecithin-buffer micellar system is shown in FIG. 2, indicating that this system phase separates at below 45° C.

To measure the protein partition coefficient, $K_p$, as defined earlier, buffered solutions containing known concentrations of either $C_{10}E_4$ or $C_8$-lecithin and one protein species were prepared and subsequently allowed to equilibrate at a constant temperature for at least 6 hours. The two phases were then withdrawn with great care using syringe and needle sets to avoid mixing of the two phases. The protein concentration in each phase was then determined using UV/visible absorbance measurements.

FIG. 3 shows the experimentally measured partition coefficient, $K_p$, of cytochrome c (▲), ovalbumin (●), and catalase (■) as a function of temperature over the range 18.8° C.–21.2° C. in the two-phase $C_{10}E_4$-buffer systems containing 0.25 g/L cytochrome c, 0.5 g/L ovalbumin, and 0.5 g/L catalase, respectively.

The fact that $K_p<1$ indicates that these three hydrophilic proteins partition preferentially into the bottom micelle-poor phase. It is also clear that as the temperature increases away from the critical temperature $T_c \approx 18.8°$ C. (corresponding to the minimum of the coexistence curve in FIG. 1), $K_p$ decreases and deviates further from unity for all three proteins. These observations suggest that: (i) proteins are pushed into that phase which has a larger available free volume (which in this case is the bottom micelle-poor phase), (ii) this tendency becomes stronger as $(T-T_c)$ increases, that is, with increasing difference in the surfactant concentrations (or the volume fractions occupied by micelles) of the two coexisting phases (see FIG. 1), and (iii) at a fixed temperature, the extent of protein partitioning into the bottom micelle-poor phase is in the order cytochrome c<ovalbumin<catalase, exactly in the same order as the protein sizes, since catalase has the largest size (M.W. 232,000 Da), followed by ovalbumin (M.W. 44,000 Da), and cytochrome c (M.W. 12,400 Da), indicating that bigger protein molecules exhibit more uneven partitioning behavior. These observations are consistent with the notion that excluded-volume interactions between proteins and $C_{10}E_4$ micelles play the dominant role in the observed partitioning behavior.

Theoretical Results and Comparison with Experimental Data.

According to the excluded-volume theoretical model, in a two-phase aqueous micellar system containing cylindrical micelles and globular hydrophilic proteins, the partition coefficient, $K_p$, is given by:

$$K_p = \exp[-(\phi_t - \phi_b)(1 + R_p/R_0)^2] \qquad (1)$$

where $\phi_t$ and $\phi_b$ are the surfactant volume fractions in the top and bottom phases respectively, $R_p$ is the protein hydrodynamic radius, and $R_0$ is the cross-sectional radius of the cylindrical micelles. It is interesting to note that, if the shape of the micelles present in the two-phase system is spherical instead of cylindrical, $K_p$ is given by:

$$K_p = \exp[-(\phi_t - \phi_b)(1 + R_p/R_0)^3] \qquad (2)$$

where $R_0$ is the radius of the spherical micelles. (Nikas, et al., *Macromolecules*, 25, 4797–4806, 1992)

Equations (1) and (2) indicate that the uneven partitioning of a hydrophilic protein in the two-phase aqueous micellar system is a direct consequence of the difference in the surfactant concentrations in the two coexisting micellar solution phases, that is, the $(\phi_t-\phi_b)$ term. In addition, the value of the partition coefficient depends on the relative sizes of micelles and proteins, as reflected in the values of $R_0$ and $R_p$. In Equations (1) and (2), the major difference is in the power of the $(1+R_p/R_0)$ term, which is 2 for cylindrical micelles and 3 for spherical micelles. This implies stronger excluded-volume interactions induced by spherical micelles as compared to cylindrical ones, and vividly illustrates the effect of micellar shape and size on the resulting protein partitioning behavior.

In order to predict the variation of $K_p$ with temperature, values of $R_0$ and $R_p$ and of $(\phi_t-\phi_b)$ as a function of temperature are needed. In general, $R_0$ is approximately equal to the length of the surfactant molecule. Calculations based on a recently developed molecular model of micellization (Puvvada and Blankschtein, *J. Chem. Phys.*, 92, 3710–3724, 1990; Naor et al., *J. Phys. Chem.*, 96, 7830–7832, 1992) yield $R_0 \approx 21$ Å for both $C_{10}E_4$ and $C_8$-lecithin. The hydrodynamic radii of cytochrome c, ovalbumin, and catalase are $R_p=19$, 29, and 52 Å, respectively (Abbott et al., *Bioseparation*, 1, 191–225, 1990). Values of $(\phi_t-\phi_b)$ at various temperatures can be obtained from the experimentally measured coexistence curves of the $C_{10}E_4$ or $C_8$-lecithin aqueous micellar systems (see FIGS. 1 and 2). In the case of the $C_{10}E_4$ micellar system, at a given temperature, $\phi_t$ and $\phi_b$ are given by the intersections of the horizontal tie line corresponding to that temperature with the concentrated and dilute branches of the coexistence curve respectively.

FIG. 3 shows the predicted variation of $K_p$ with temperature in the $C_{10}E_4$-buffer two-phase micellar system for cytochrome c (dotted line), ovalbumin (dashed line), and catalase (full line), using $R_0 \approx 21$ Å, the $R_p$ values listed above, and the corresponding $(\phi_t-\phi_b)$ values determined from FIG. 1 for each temperature. Note that these predictions are based on Equation (1), since $C_{10}E_4$ forms cylindrical micelles in aqueous solutions. As can be seen, there is good agreement with the experimentally measured $K_p$ values, thus strongly supporting the theory that excluded-volume interactions between proteins and micelles are responsible for the observed preferential protein partitioning into the micelle-poor phase.

The dependence of the partition coefficient, $K_p$, on protein size, $R_p$, can be seen clearly by plotting $K_p$ as a function of the ratio, $R_p/R_0$ at a fixed temperature, or equivalently, at a fixed $(\phi_t-\phi_b)$ value. Specifically, for $C_{10}E_4$ at 21° C., $\phi_t-\phi_b \approx 10\%$ (see FIG. 1). FIG. 4 shows the predicted variation of $K_p$ as a function of $R_p/R_0$ (full line), together with the experimental $K_p$ values corresponding to cytochrome c (▲), soybean trypsin inhibitor (♦), ovalbumin (●), bovine serum albumin (▼), and catalase (■). The hydrodynamic radii of soybean trypsin inhibitor and bovine serum albumin are $R_p$=22 Å and 36 Å, respectively (Dubin and Principi, *J. Chromatogr.*, 479, 159–164, 1989). This figure indicates that, as $R_p$ increases relative to $R_0$, the value of $K_p$ decreases and can become vanishingly small for $R_p/R_0 > 5$.

In the case of $C_8$-lecithin, for illustrative purposes, we selected a temperature of 10° C., at which $(\phi_b-\phi_t)=10\%$. Note that in the $C_8$-lecithin case, the bottom phase is micelle-rich while the top phase is micelle-poor. Accordingly, due to excluded-volume interactions, hydrophilic proteins should partition preferentially into the top micelle-poor phase, namely, the values of $K_p$ should be greater than 1. FIG. 5 shows the predicted variation of $K_p$ as a function of $R_p/R_0$ using Equation 1, together with the experimental $K_p$ values corresponding to cytochrome c (▲), ovalbumin (●), and catalase (■). This figure shows that, as predicted by the excluded-volume theory, K>1 and increases as $R_p/R_0$ increases. One can see from FIGS. 4 and 5 that the agreement between the excluded-volume theory and the partitioning experiments is good for both micellar systems.

EXAMPLE 2
Partitioning of Virus Particles in Two-Phase Aqueous Micellar Systems.

The partitioning behavior of virus particles, which are much larger in size than protein molecules, in two-phase aqueous micellar systems was investigated for the first time. Homogeneous $C_{10}E_4$, as mentioned in Example 1, was used to generate the two-phase system. The virus particles used in the partitioning experiments were bacteriophages (or phages), and the partitioning behavior of three bacteriophages, including $\phi$X174, P22, and T4, was investigated. The radii of these three bacteriophages are 125 Å, 300 Å, and about 700 Å, respectively, indeed much larger than the radii of typical protein molecules. pH 7 McIlvaine buffer was used to maintain the solution pH. The phage concentrations in the solutions were determined using a biological activity assay, in which phage solutions were incubated with host bacteria to generate phage plaques, and the phage concentrations were calculated from the numbers of plaques. The host bacteria of both $\phi$X174 and T4 are *Escherichia coli* B, and that of P22 is Salmonella.

The coexistence curve of the $C_{10}E_4$-buffer micellar system was determined without and with added virus particles. The results, shown in FIG. 6, indicate that the presence of virus particles at such relative low concentrations does not influence the phase separation equilibrium of the $C_{10}E_4$ micellar system. We have also shown that the presence of $C_{10}E_4$ micelles in the solutions does not interfere with the biological activity assay for virus concentration determination.

The virus partition coefficient, $K_v$, was measured using buffered solutions containing known concentrations of $C_{10}E_4$ surfactant and one of the three viruses (at a concentration of about $10^8$ particles/mL). The mixture was allowed to equilibrate at a constant temperature for about 4 hours (in the case of partitioning $\phi$X174 and T4) or at least 8 hours (in the case of partitioning P22). The virus concentrations in the two phases were determined using the biological activity assay.

FIG. 7 shows the experimentally measured virus partition coefficient, $K_v$, of $\phi$X174 (Δ), P22 (□), and T4 (○) as a function of temperature over the range of 18.8°–21.2° C. The $K_v$ values are all smaller than 1, indicating the preference of the viruses to partition into the bottom micelle-poor phase. In addition, the $K_v$ of $\phi$X174 decreases with increasing temperature, reaching $2 \times 10^{-3}$ at 21° C., while those of P22 and T4 primarily remain at about $10^{-3}$ over this temperature range. As compared to the partition coefficients of proteins, as shown in FIG. 3, which are of order 1, the virus particles exhibit more drastic partitioning behavior than proteins, suggesting that more promising results can be achieved for the purposes of separation or concentration of viruses.

EXAMPLE 3
Unequal Volume Partitioning in Two-Phase Aqueous Micellar Systems for Viral Clearance and Concentration.

The efficiency of removal or concentration of viruses from a solution containing hydrophilic proteins can be enhanced by varying the volume ratio of the two coexisting micellar phases. The volumes of the two phases can be manipulated by changing the total surfactant concentration of the solution according to the lever rule, which provides a quantitative relationship between the volume ratio and the surfactant concentrations of the two coexisting phases, using the principle of mass balance.

The removal and concentration of the virus P22 from a solution containing the hydrophilic protein ovalbumin were achieved as follows: The hydrophilic protein ovalbumin and the virus P22 were both introduced into the two-phase aqueous $C_{10}E_4$ system, at overall concentrations of 0.62 g/L and $4.7 \times 10^7$ virus particles/mL respectively. pH 7 McIlvaine buffer was used to maintain the solution pH. The protein and virus were allowed to partition between the two coexisting phases by keeping the system at a fixed temperature of 20.1° C. for about 24 hours to ensure that thermal and phase separation equilibrium was indeed established. Samples from each phase were extracted with great care using syringes, and the protein and virus concentrations in each sample were determined. The ovalbumin concentration was determined using UV absorbance measurements at 280 nm, as mentioned in Example 1, and the virus concentration was determined using the biological activity assay, as mentioned in Example 2.

The results of the partitioning experiments are illustrated schematically in FIG. 8 and summarized in more detail in Table 1. The data reported in FIG. 8 and Table 1 represent average values of three sets of experiments all conducted at 20.1° C. and an overall $C_{10}E_4$ concentration of 7.5 wt %. FIG. 8 indicates that both the protein and the virus partition preferentially into the micelle-poor phase, as reflected by the fact that the final concentrations of both species in this phase are higher than those in the micelle-rich phase. However, while the final protein concentrations in each of the two phases are of the same order of magnitude (0.54 g/L versus 1.05 g/L, see Table 1), those of the virus differ considerably by about three orders of magnitude ($3.7 \times 10^6$ virus particles/mL versus $6.7 \times 10^8$ virus particles/mL, see Table 1). These results clearly support our earlier predictions that the virus should partition much more extremely than the protein into the micelle-poor phase. As shown in Table 1, the partition coefficient of the protein ovalbumin is about 0.5, while that of the virus P22 is about $6 \times 10^{-3}$, indicating the extreme partitioning of P22 into the micelle-poor phase as compared to that of ovalbumin.

To further quantify the separation and concentration efficiencies, two parameters are defined:
(1) Yield in the Top Phase, Y Y is defined as the amount of a solute which can be retrieved from the top phase relative to the total amount of the solute in the solution, namely, $$Y\ (\%) = [C_t V_t / (C_t V_t + C_b V_b)] \times 100\ (\%)$$

where $V_t$ and $V_b$ are the volumes of the top (micelle-rich) and bottom (micelle-poor) phases respectively. The yield, Y, provides a measure of the amount of a species that can be retrieved or obtained from the micelle-rich phase.
(2) Concentration Factor in the Bottom Phase, $\alpha$ $\alpha$ is defined as the ratio of the concentration of a solute in the bottom (micelle-poor) phase, $C_b$, to its original concentration in the solution, $C_{orig}$, namely, $$\alpha = C_b / C_{orig}$$

The concentration factor, $\alpha$, provides a measure of the concentration efficiency of a solute species.

The yield data in Table 1 indicate that, after a single partitioning stage, about 84% of the protein can be retrieved from the micelle-rich phase, with only about 8% of the virus remaining in that phase. This indicates that this operation can indeed remove most of the virus while retaining the majority of the protein in one of the two coexisting phases. In other words, our first goal of clearing viruses from a solution containing a desired biomaterial can be achieved.

On the other hand, the concentration factor data in Table 1 indicate that, after a single partitioning stage, this operation can increase the virus concentration in the micelle-poor phase by more than 10 times, while that of the protein does not increase significantly. This indicates that virus particles were indeed pushed into the small micelle-poor phase. Hence, our second goal of concentrating viruses can also be achieved.

Although certain preferred embodiments of the present invention have been described, the spirit and scope of the invention is by no means restricted to what is described above.

TABLE 1

Summary of Experimental Results of Partitioning Protein (Ovalbumin) and Virus (P22) in a Two-Phase Aqueous $C_{10}E_4$ Micellar System.

Experimental Conditions:

| | |
|---|---|
| Temperature | 20.1 ± 0.02° C. |
| Overall $C_{10}E_4$ Concentration | 7.5 wt % |
| Equilibration Time | 21 Hours |
| Final Volume Ratio ($V_t/V_b$) | 14.5 |

TABLE 1-continued

Summary of Experimental Results of Partitioning Protein (Ovalbumin) and Virus (P22) in a Two-Phase Aqueous $C_{10}E_4$ Micellar System.

Results:

| | Ovalbumin | P22 |
|---|---|---|
| Original Concentration | 0.62 g/L | $4.7 \times 10^7$ virus particles/mL |
| Final Concentration: Top | 0.54 g/L | $3.7 \times 10^6$ virus particles/mL |
| Final Concentration: Bottom | 1.05 g/L | $6.7 \times 10^8$ virus particles/ |
| Partition Coefficient, K | 0.51 | $5.7 \times 10^{-3}$ |
| Yield in the Top Phase, Y (%) | 84.48 | 7.64 |
| Concentration Factor in the Bottom Phase, $\alpha$ | 1.68 | 14.05 |

EXAMPLE 4

Removal of Virus Particles in a Three-Stage Process.

In order to further facilitate the removal and concentration of large biological particles (such as viruses or cells) from a desired bioproduct (such as proteins), a multi-stage operation can be designed. This approach should yield an increased efficiency of virus removal in the top (micelle-rich) phase.

In this example, a single protein and virus species are partitioned in the two phase aqueous $C_{10}E_4$ system having an initial solution volume of 16 L, containing the protein at 500 mg/L, the virus at $10^{11}$ virus particles/L, and the surfactant. The partition coefficients of the protein and the virus are 0.5 and $10^{-3}$ respectively at the chosen operating conditions. The amount of surfactant is chosen so as to make the final volume ratio of the two coexisting phases, $V_t/V_b$, equal to 15 at each partitioning stage. In each subsequent partitioning stage, the top (micelle-rich) phase of the previous stage is treated and partitioned again to reach the final volume ratio of $V_t/V_b=15$. This can be achieved by changing the operating conditions, including varying temperature or adding salts.

Based on the mass-balance principle, that is, $$C_t V_t + C_b V_b = C_{orig} (V_t + V_b)$$

and on the relation $$K = \frac{C_t}{C_b}$$

$C_t$ and $C_b$ can be calculated from the known values of $C_{orig}$, $V_t$, $V_b$, and K. Note that the symbols $C_t$, $C_b$, $C_{orig}$, $V_t$, and $V_b$ were defined in Example 3.

The protein yield in the top phase and the virus removal ratio in the top phase were calculated. Results for a three-stage operation corresponding to the above parameter values permit retrieval of 88.2% of protein and attainment of 1.8 logs of virus removal in the first of the three stages, retrieval of 77.9% of protein and attainment of 3.6 logs of virus removal in the second of the three stages, and retrieval of 68.7% of protein and attainment of 5.4 logs of virus removal in the last stage; the results at each stage being presented below:

1. First Stage:
$V_t = 15L$, $V_b = 1L$, Total $V = 16L$, $V_t/V_b = 15$

|        | Protein Concentration (mg/L) | Virus Concentration (1/L) | Amount of Protein (mg) | Overall Protein Yield (%) |
|--------|------|------|------|------|
| TOP    | 470.59 | $1.58 \times 10^9$ | 7058.85 | 88.2 |
| BOTTOM | 941.18 | $1.58 \times 10^{12}$ | 941.18 | |

$$\text{Virus Removal Ratio} = \frac{C_{virus,\,t}}{C_{virus,\,orig}} = 1.58 \times \frac{10^9}{10^{11}} = 1.58 \times 10^{-2} = 1.80 \text{ logs}$$

2. Second Stage: Treating the TOP phase of the first stage
$V_t = 14.0625L$, $V_b = 0.9375L$, Total $V = 15L$, $V_t/V_b = 15$

|        | Protein Concentration (mg/L) | Virus Concentration (1/L) | Amount of Protein (mg) | Overall Protein Yield (%) |
|--------|------|------|------|------|
| TOP    | 442.91 | $2.48 \times 10^7$ | 6228.42 | 77.9 |
| BOTTOM | 885.81 | $2.48 \times 10^{10}$ | 830.45 | |

$$\text{Virus Removal Ratio} = \frac{C_{virus,\,t}}{C_{virus,\,orig}} = 2.48 \times \frac{10^7}{10^{11}} = 2.48 \times 10^{-4} = 3.60 \text{ logs}$$

3. Third Stage: Treating the TOP phase of the second stage
$V_t = 13.1836L$, $V_b = 0.8789L$, Total $V = 14.0625L$, $V_t/V_b = 15$

|        | Protein Concentration (mg/L) | Virus Concentration (1/L) | Amount of Protein (mg) | Overall Protein Yield (%) |
|--------|------|------|------|------|
| TOP    | 416.85 | $3.92 \times 10^5$ | 5495.58 | 68.7 |
| BOTTOM | 833.71 | $3.92 \times 10^8$ | 732.75 | |

$$\text{Virus Removal Ratio} = \frac{C_{virus,\,t}}{C_{virus,\,orig}} = 3.92 \times \frac{10^5}{10^{11}} = 3.92 \times 10^{-6} = 5.41 \text{ logs}$$

The results presented above demonstrate that by repeating the same operation three times at the same final volume ratio, 5 logs of virus removal can be attained. These results clearly show the potential of utilizing two-phase aqueous micellar systems to attain the desired virus removal efficiency.

EXAMPLE 5
Removal of Virus Particles in a Two-Stage Process.

It is predicted that if the partition coefficient of the virus is reduced from $10^{-3}$ to $10^{-5}$ using the assumptions outlined above, the virus removal efficiency in a two-stage operation will be considerably increased, assuming that the protein partition coefficient remains the same. Indeed, if the partition coefficient is reduced below $10^{-5}$, a remarkable virus removal efficiency could be attained in a single-stage operation. In the two-stage separation described below, the first stage results in retrieval of 88.2% of protein and attainment of 3.8 logs of virus removal, and the second stage results in retrieval of 77.9% of protein and attainment of 7.6 logs of virus removal, as reflected in the following two-stage calculations:

1. First Stage:
$V_t = 15L$, $V_b = 1L$, Total $V = 16L$, $V_t/V_b = 15$

|        | Protein Concentration (mg/L) | Virus Concentration (1/L) | Amount of Protein (mg) | Overall Protein Yield (%) |
|--------|------|------|------|------|
| TOP    | 470.59 | $1.60 \times 10^7$ | 7058.85 | 88.2 |
| BOTTOM | 941.18 | $1.60 \times 10^{12}$ | 941.18 | |

$$\text{Virus Removal Ratio} = \frac{C_{virus,\,t}}{C_{virus,\,orig}} = 1.60 \times \frac{10^7}{10^{11}} = 1.60 \times 10^{-4} = 3.80 \text{ logs}$$

2. Second Stage: Treating the TOP phase of the first stage
$V_t = 14.0625L$, $V_b = 0.9375L$, Total $V = 15L$, $V_t/V_b = 15$

|        | Protein Concentration (mg/L) | Virus Concentration (1/L) | Amount of Protein (mg) | Overall Protein Yield (%) |
|--------|------|------|------|------|
| TOP    | 442.91 | $2.56 \times 10^3$ | 6228.37 | 77.9 |
| BOTTOM | 885.81 | $2.56 \times 10^8$ | 830.45 | |

$$\text{Virus Removal Ratio} = \frac{C_{virus,\,t}}{C_{virus,\,orig}} = 2.56 \times \frac{10^3}{10^{11}} = 2.48 \times 10^{-8} = 7.59 \text{ logs}$$

We claim:

1. A method for size separating a mixture of reagents including an analyte and at least one contaminant of different size, comprising:
   (a) providing at least one surfactant, the surfactant being capable under selected conditions of forming a two-phase aqueous micellar system having a micelle-rich phase and a micelle-poor phase
   (b) forming the two-phase aqueous micellar system containing surfactant as specified in (a) in the presence of the mixture of reagents; and
   (c) forming conditions for driving the majority of the larger reagent in the mixture into the aqueous domain of the micelle-poor phase and the majority of the smaller reagents in the mixture into the aqueous domain of the micelle-rich phase.

2. A method according to claim 1, wherein the analyte is hydrophilic.

3. A method according to claim 1, wherein the reagent migrates into the micelle-poor phase to an extent which depends on the size of the reagent.

4. A method according to claim 3, wherein the extent of migration of selected reagents is retarded in the presence of an affinity binding ligand associated with the micelles.

5. A method according to claim 4, wherein the ligand is capable of binding the reagent by means of an ionic linkage or a non-ionic linkage.

6. A method according to claim 1, wherein the contaminant is an environmental pollutant.

7. A method according to claim 6, wherein the environmental pollutant is selected from the group consisting of metal ions, radioactive contaminants, and synthetic organic materials.

8. A method according to claim 1, wherein the analyte is a biological material.

9. A method according to claim 8, wherein the biological material is selected from the group consisting of bacteria, viruses, cells, cell organelles, blood product, protein aggregates, dispersed proteins, and nucleic acids.

10. A method according to claim 8, wherein the biological material is a hydrophilic protein.

11. A method according to claim 8, wherein the biological material is a pathogen.

12. A method according to claim 8, wherein the biological material is a blood product.

13. A method according to claim 8, wherein the analyte is a virus for use in vaccine production or as a vehicle for gene therapy.

14. A method according to claim 1, wherein the analyte is a colloidal particle.

15. A method according to claim 1, wherein step (b) further comprises obtaining a final concentration of surfactant in the range of 1–30 wt % of solution.

16. A method according to claim 1, wherein step (b) further comprises selecting a temperature up to the boiling point of the surfactant solution at atmospheric pressure.

17. A method according to claim 16, wherein the temperature is in the range of 4°–50° C.

18. A method according to claim 1, wherein step (b) further comprises selecting a pH in the range of 2–12.

19. A method according to claim 1, wherein step (b) further comprises adding at least one salt selected from the group consisting of alkali salts, phosphate, sulphate, citrate, and nitrate salts.

20. A method according to claim 19, wherein the salt has a final concentration in the range of 0–5M.

21. A method according to claim 19, wherein the surfactant is n-decyl tetra(ethylene oxide).

22. A method according to claim 21, wherein the salt concentration is in the range of 0–5M.

23. A method according to claim 22, wherein the conditions of step (a) further comprises obtaining a final concentration of n-decyl tetra(ethylene oxide) in the range of 1–8 wt %.

24. A method according to claim 22, wherein the conditions of step (a) further comprise selecting a temperature below 100° C.

25. A method according to claim 22, wherein step (b) further comprises selecting a pH in the range of 5–9.

26. A method according to claim 19, wherein the surfactant is dioctanoyl phosphatidylcholine.

27. A method according to claim 26, wherein the salt has a final concentration in the range of 0–5M.

28. A method according to claim 27, wherein step (b) further comprises obtaining a final concentration of dioctanoyl phosphatidylcholine in the range 1–10 wt %.

29. A method according to claim 27, wherein step (b) further comprises selecting a temperature below 100° C.

30. A method according to claim 27, wherein step (b) further comprises selecting a pH in the range of 5–9.

31. A method according to claim 1, wherein the surfactant of step (a) is a non-ionic surfactant.

32. A method according to claim 31, wherein the non-ionic surfactant is an alkyl poly(ethylene oxide).

33. A method according to claim 32, wherein the alkyl poly(ethylene oxide) surfactant is n-decyl tetra(ethylene oxide).

34. A method according to claim 1, wherein the surfactant of step (a) is a zwitterionic surfactant.

35. A method according to claim 34, wherein the zwitterionic surfactant is dioctanoyl phosphatidylcholine.

36. A method according to claim 1, further comprising forming the micellar system using two or more surfactants.

37. A method according to claim 36, wherein the surfactants are non-ionic surfactants.

38. A method according to claim 36, wherein the surfactants comprise at least one non-ionic surfactant and at least one ionic surfactant.

39. A method according to claim 38, wherein the ionic surfactant is positively charged.

40. A method according to claim 38, wherein the ionic surfactant is negatively charged.

41. A method according to claim 36, wherein the surfactants comprise at least one non-ionic and one zwitterionic surfactant.

42. A method according to claim 36, wherein the surfactants comprise at least one zwitterionic and one ionic surfactant.

43. A method according to claim 42, wherein the ionic surfactant is negatively charged.

44. A method according to claim 42, wherein the ionic surfactant is positively charged.

45. A method according to claim 36, wherein the surfactants are zwitterionic surfactants.

46. A method according to claim 1, wherein the shape of individual micelles is cylindrical.

47. A method according to claim 1, wherein the shape of individual micelles is spherical.

48. A method according to claim 1, wherein a selected condition of step (a) includes combining at least one type of polymer with the surfactant for enhancing the separation of the analyte.

49. A method according to claim 48, wherein the polymer type is a non-ionic polymer.

50. A method according to claim 48, wherein the polymer type is an ionic polymer.

51. A method according to claim 48, wherein step (a) includes combining at least one ionic polymer type and at least one non-ionic polymer type with the surfactant for enhancing the size separation of the analyte away from the contaminant.

52. A method according to claim 1, wherein step (c) further comprises: collecting the phase containing the at least partially separated analyte and repeating steps (a) through (c) so as to further separate analyte from contaminating materials.

53. A method according to claim 1, wherein step (c) further comprises: collecting the phase containing at least partially separated contaminating material and repeating steps (a) through (c) so as to separate the residual analyte therein.

54. A method according to claim 1, wherein the analyte is virus and the contaminating material is any of hydrophilic proteins, hydrophilic protein aggregates, nucleic acids, cell organelles, cell debris and blood products.

55. A method according to claim 1, wherein the analyte is selected from the group consisting of hydrophilic proteins, hydrophilic protein aggregates, nucleic acids, cell organelles, cell debris and blood products and the contaminating material is virus.

56. A method according to claim 52, wherein the analyte is virus and the contaminating material is selected from the group consisting of protein, nucleic acid, cell debris and blood products.

57. A method according to claim 52, wherein the analyte is selected from the group consisting of protein, nucleic acid, cell debris and blood products and the contaminating material is virus.

58. A method according to claim 53, wherein the analyte is virus and the contaminating material is selected from the group consisting of protein, nucleic acid, cell debris and blood products.

59. A method according to claim 53, wherein the analyte is selected from the group consisting of protein, nucleic acid, cell debris and blood products and the contaminating material is virus.

60. A method according to claim 1, wherein the analyte is virus, the contaminating material is hydrophilic protein, the surfactant is n-decyl tetra(ethylene oxide), the final concentration of n-decyl tetra(ethylene oxide) is in the range of 7–8 wt %, the temperature of the two-phase aqueous micellar system is in the range of 20°–22° C., and the pH is in the range of 6–8.

61. A method according to claim 1, wherein the analyte is hydrophilic protein, the contaminating material is virus, the surfactant is n-decyl tetra(ethylene oxide) the final concentration of n-decyl tetra(ethylene oxide) is in the range of 7–8 wt %, the temperature of the two-phase aqueous micellar system is in the range of 20°–22° C., and the pH is in the range of 6–8.

62. A method according to claim 1, wherein step (b) further comprises forming the two-phase aqueous micellar system such that one of the two phases has a smaller volume than the other phase; and step (c) further comprises allowing the analyte and contaminating material to partition unevenly causing the majority of the analyte to reside in the smaller-volume phase.

63. A method according to claim 1, wherein step (b) further comprises forming the two-phase aqueous micellar system such that one of the two phases has a smaller volume than the other phase; and step (c) further comprises allowing the analyte and contaminating material to partition unevenly causing the majority of the analyte to reside in the larger-volume phase.

64. A method for purifying virus from a mixture containing contaminants; comprising:
   (a) providing at least one surfactant, the surfactant being capable under selected conditions of forming a two-phase aqueous micellar system having a micelle-rich phase and a micelle-poor phase;
   (b) forming the two-phase aqueous micellar system containing surfactant as specified in (a) in the presence of the mixture of reagents; and
   (c) forming conditions for driving the majority of the virus in the mixture into the aqueous domain of the micelle-poor phase and the majority of the contaminant in the mixture into the aqueous domain of the micelle-rich phase.

65. A method according to claim 64, comprising step (d) of repeating steps (a)–(c) until the virus is substantially pure.

\* \* \* \* \*

UNITED STATES PATENT AND TRADEMARK OFFICE
CERTIFICATE OF CORRECTION

PATENT NO. : 5,772,888
DATED : June 30, 1998
INVENTOR(S) : Chia-Li Liu, et. al.

It is certified that error appears in the above-identified patent and that said Letters Patent is hereby corrected as shown below:

Title page, item [54] after the Title, insert

-- This invention was made with government support under Grant Number CBT-8957143 awarded by the National Science Foundation. The government has certain rights to the invention. --

Signed and Sealed this

Seventeenth Day of November, 1998

Attest:

BRUCE LEHMAN

*Attesting Officer*      *Commissioner of Patents and Trademarks*